US00PP37570P2

(12) United States Plant Patent
Mathey

(10) Patent No.: US PP37,570 P2
(45) Date of Patent: Aug. 11, 2026

(54) ***ABELIA* PLANT NAMED 'SMNABP'**

(50) Latin Name: ***Abelia* x *grandiflora***
Varietal Denomination: SMNABP

(71) Applicant: Megan M. Mathey, Holland, MI (US)

(72) Inventor: Megan M. Mathey, Holland, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 19/383,640

(22) Filed: Nov. 8, 2025

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP35,470 P2 * 11/2023 Dirr ..... Plt./226

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Abelia* plant named 'SMNABP', characterized by its compact, upright to outwardly spreading and uniformly mounding plant habit; vigorous growth habit; freely branching habit; dense and bushy appearance; red-colored stems and peduncles; dark green-colored leaves; freely flowering habit; nodding to drooping salverform flowers that are light pink-colored petals and pinkish red-colored sepals; and good container and garden performance.

3 Drawing Sheets

Figure 1:
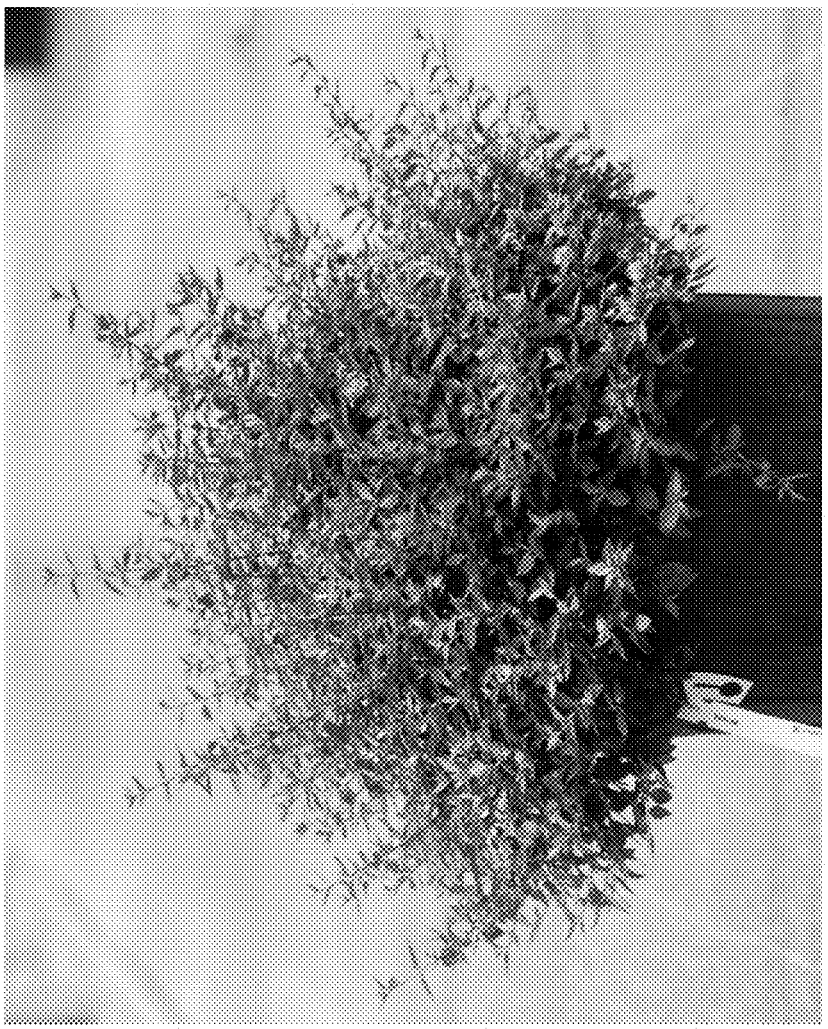

Botanical designation: *Abelia* x *grandiflora*.
Cultivar denomination: 'SMNABP'.

BACKGROUND OF THE INVENTION

The present invention relates to a new and distinct cultivar of *Abelia* plant, botanically known as *Abelia* x *grandiflora*, commonly referred to as Glossy *Abelia* and hereinafter referred to by the name 'SMNABP'.

The new *Abelia* is a product of a planned breeding program conducted by the Inventor in Grand Haven, Michigan. The objective of the breeding program was to develop new uniform and freely branching *Abelia* plants with unique leaf and flower coloration.

The new *Abelia* plant originated from an open-pollination during the summer of 2017 of *Abelia* x *grandiflora* 'Bobbie', not patented, as the female, or seed, parent with an unknown proprietary selection of *Abelia* x *grandiflora* as the male, or pollen, parent. The new *Abelia* plant was discovered and selected by the Inventor during the summer of 2020 as a single flowering plant within the progeny of the stated open-pollination in a controlled environment in Grand Haven, Michigan.

Asexual reproduction of the new *Abelia* plant by softwood cuttings in a controlled greenhouse environment in Grand Haven, Michigan since the summer of 2020 has shown that the unique features of this new *Abelia* plant are stable and reproduced true to type in successive generations of asexual reproduction.

SUMMARY OF THE INVENTION

Plants of the new *Abelia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNABP'. These characteristics in combination distinguish 'SMNABP' as a new and distinct *Abelia* plant:

1. Compact, upright to outwardly spreading and uniformly mounding plant habit.
2. Vigorous growth habit.
3. Freely branching habit; dense and bushy appearance.
4. Red-colored stems and peduncles.
5. Dark green-colored leaves.
6. Freely flowering habit.
7. Nodding to drooping salverform flowers that are light pink-colored petals and pinkish red-colored sepals.
8. Good container and garden performance.

Plants of the new *Abelia* can be compared to plants of the female parent, 'Bobbie'. In side-by-side comparisons, plants of the new *Abelia* differ primarily from plants of 'Bobbie' in the following characteristics:

1. Plants of the new *Abelia* are more compact than plants of 'Bobbie'.
2. Plants of the new *Abelia* are more freely branching, denser and bushier than plants of 'Bobbie'.
3. Plants of the new *Abelia* are more uniformly mounded than and not as rangy as plants of 'Bobbie'.

Plants of the new *Abelia* can also be compared to plants of *Abelia* x *grandiflora* 'Edward Goucher', not patented. In side-by-side comparisons, plants of the new *Abelia* differ primarily from plants of 'Edward Goucher' in the following characteristics:

1. Plants of the new *Abelia* are more uniformly mounded than and not as rangy as plants of 'Edward Goucher'.
2. Flowers of plants of the new *Abelia* have two to four sepals whereas flowers of plants of 'Edward Goucher' have two sepals.
3. Flower sepals of plants of the new *Abelia* are oblong in shape whereas flower sepals of plants of 'Edward Goucher' are elliptic in shape.

BRIEF DESCRIPTION OF THE PHOTOGRAPHS

The accompanying colored photographs illustrate the overall appearance of the new *Abelia* plant showing the colors as true as it is reasonably possible to obtain in colored reproductions of this type. Colors in the photographs may differ slightly from the color values cited in the detailed botanical description which accurately describe the colors of the new *Abelia* plant.

The photograph on the first sheet (FIG. 1) is a side perspective view of a typical vegetative (prior to flowering) plant of 'SMNABP' grown in a container.

Figure 2:
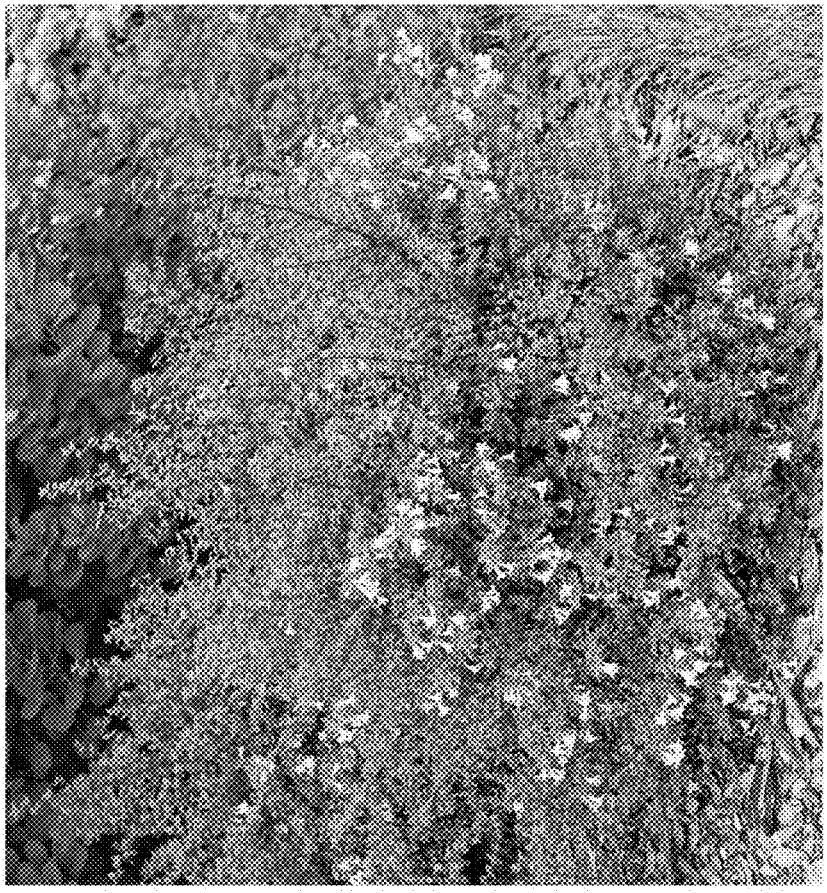

The photograph on the second sheet (FIG. 2) is a side perspective view of typical flowering plant of 'SMNABP' grown in an outdoor nursery during the summer.

Figure 3:
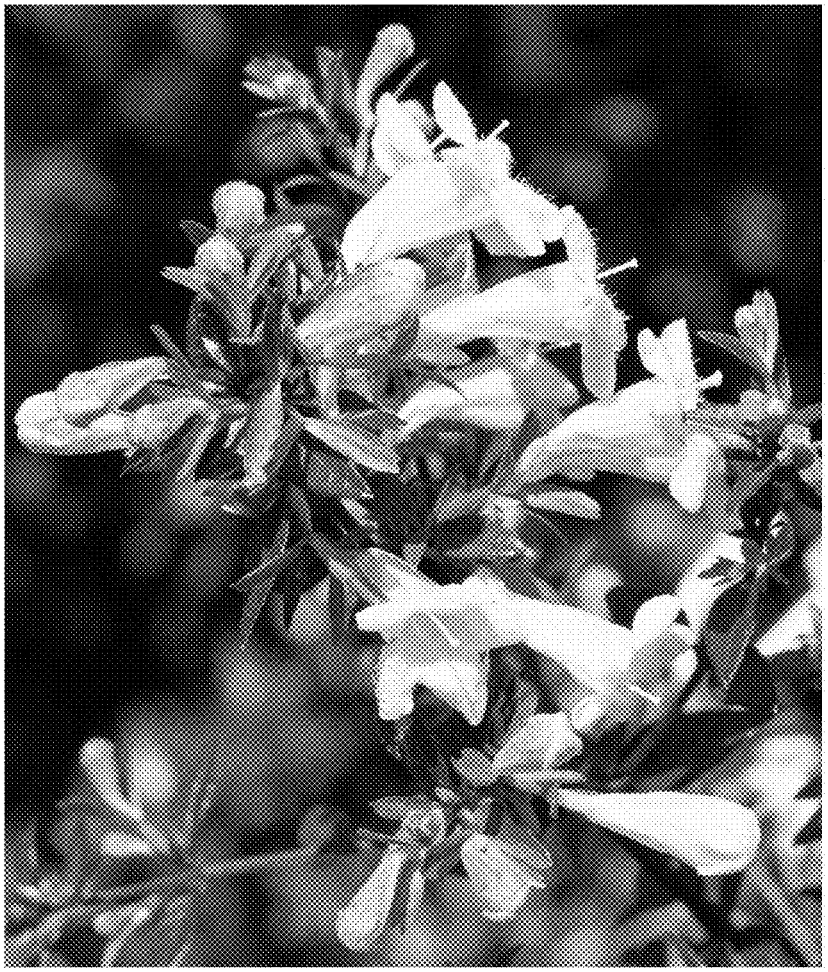

The photograph on the third sheet (FIG. 3) is a close-up view of a typical flowering plant of 'SMNABP' grown in an outdoor nursery.

DETAILED BOTANICAL DESCRIPTION

The following observations, measurements and values describe plants grown during the summer in three-gallon containers in a polyethylene-covered greenhouse in Grand Haven, Michigan and under cultural practices typical of commercial *Abelia* production. During the production of the plants, day temperatures ranged from 18° C. to 27° C. and night temperatures ranged from 5° C. to 10° C. Plants were three years old when the detailed description was taken. In the description, color references are made to The Royal Horticultural Society Colour Chart, 2015 Edition, except where general terms of ordinary dictionary significance are used.

Botanical classification: *Abelia* x *grandiflora* 'SMNABP'.

Parentage:

*Female, or seed, parent.*—*Abelia* x *grandiflora* 'Bobbie', not patented.

*Male, or pollen, parent.*—Unknown proprietary selection of *Abelia* x *grandiflora*, not patented.

Propagation:

*Type.*—By softwood cuttings.

*Time to produce a rooted young plant, summer.*—About 40 days at temperatures ranging from 18° C. to 27° C.

*Root description.*—Fine, fleshy and fibrous; typically white to tan in color, actual color of the roots is dependent on substrate composition, water quality, fertilizer, substrate temperature and physiological age of roots.

*Rooting habit.*—Freely branching habit; medium density.

Plant description:

*Plant form and growth habit.*—Perennial shrub; compact, upright to outwardly spreading and uniformly mounding plant habit; vigorous growth habit and moderate to rapid growth rate.

*Branching habit.*—Freely branching habit, dense and bushy growth habit with about 12 to 15 primary lateral branches each with about 20 to 25 secondary lateral branches developing per plant.

*Plant height.*—About 40 cm.

*Plant diameter* (*area of spread*).—About 75 cm.

Lateral branch description:

*Length, primary lateral branches.*—About 45 cm.

*Diameter, primary lateral branches.*—About 4 mm.

*Length, secondary lateral branches.*—About 10 cm.

*Diameter, secondary lateral branches.*—About 2 mm.

*Internode length.*—About 2 cm.

*Strength.*—Moderately strong to strong.

*Aspect.*—Erect to about 60° from vertical.

*Texture and luster, developing.*—Smooth glabrous; matte; becoming woody with development.

*Color, when developing and fully developed.*—Close to 178A; when woody, close to 200B and 199B.

Leaf description:

*Arrangement.*—Opposite, simple.

*Length.*—About 2 cm.

*Width.*—About 1 cm.

*Shape.*—Ovate.

*Apex.*—Acute.

*Base.*—Obtuse.

*Margin.*—Serrate; serrations are widely spaced and shallow.

*Texture and luster, upper surface.*—Smooth, glabrous; semi-glossy.

*Texture and luster, lower surface.*—Smooth, glabrous; matte.

*Venation pattern.*—Pinnate.

*Color.*—Developing leaves, upper surface: Close to 146A. Developing leaves, lower surface: Close to 147B to 147C. Fully expanded leaves, upper surface: Close to 147A; venation, close to 147A; leaf color does not change in the autumn. Fully expanded leaves, lower surface: Close to 147B; venation, close to 147A; leaf color does not change in the autumn.

*Petioles.*—Length: About 2 mm. Diameter: About 1 mm. Texture and luster, upper and lower surfaces: Smooth, glabrous; matte. Color, upper and lower surfaces: Close to 147B tinged with close to 178A.

Flower description:

*Flower appearance and arrangement.*—Single salver-form flowers arranged in terminal and axillary clusters; freely flowering habit with about two to six flowers per cluster and about 2,000 flowers developing per plant during the flowering season; flower aspect, nodding to drooping.

*Fragrance.*—Moderately fragrant; sweet, floral.

*Natural flowering season.*—Plants flower from July to September in Michigan; individual flowers last about one week on the plant; flowers not persistent.

*Flower buds.*—Length: About 5 mm. Diameter: About 2 mm. Shape: Obovate. Texture and luster: Smooth, glabrous; matte. Color: Close to 181C.

*Flower diameter.*—About 1.5 cm.

*Flower depth.*—About 2 cm.

*Flower throat diameter.*—About 7.5 mm.

*Flower tube length.*—About 2 cm.

*Flower tube diameter, proximally.*—About 2 mm.

*Petals.*—Quantity and arrangement: Four to five fused petals arranged in a single whorl and fused at the base into a slender tube. Lobe length: About 5 mm.

Lobe width: About 5 mm. Shape, free part: Roughly globose. Apex: Obtuse. Base: Fused. Margin: Entire; slightly undulate. Texture and luster, upper and lower surfaces, lobes: Smooth and silky, glabrous; matte. Texture, throat: Smooth, glabrous. Texture, tube: Smooth, glabrous. Color: When opening and fully opened, upper surface: Close to 69B. When opening and fully opened, lower surface: Close to 69B tinged with close to 65B.

*Sepals*.—Quantity and arrangement: Two to four sepals arranged in a single whorl. Length: About 7 mm. Width: About 2 mm. Shape: Oblong. Apex: Broadly acute. Base: Cuneate. Margin: Entire. Texture and luster, upper and lower surfaces: Smooth, glabrous; matte. Color, upper and lower surfaces: Close to 181C.

*Peduncles*.—Length: About 2 mm. Diameter: About 0.5 mm. Strength: Moderately strong. Aspect: About 45° from stem axis. Texture and luster: Smooth, glabrous; matte. Color: Close to 178B.

*Reproductive organs*.—Stamens: Quantity per flower: Four. Filament length: About 1.5 cm. Filament color: Close to NN155A. Anther size: About 2 mm by 1 mm. Anther shape: Linear. Anther color: Close to 158A. Pollen amount: Scarce to moderate. Pollen color: Close to 158A. Pistils: Quantity per flower: One. Pistil length: About 1.5 cm. Stigma shape: Globular. Stigma diameter: About 0.5 mm. Stigma color: Close to NN155A. Style color: Close to NN155A. Ovary color: Close to 178A and 144C. Seeds and fruits: To date, seed and fruit production have not been observed on plants of the new *Abelia*.

Garden performance: Plants of the new *Abelia* have been observed to have good garden performance and to tolerate rain, wind and to be suitable for USDA Zones 6 through 9.

Pathogen & pest resistance: To date, plants of the new *Abelia* have not been shown to be resistant to pathogens and pests common to *Abelia* plants.

It is claimed:

1. A new and distinct *Abelia* plant named 'SMNABP' as herein illustrated and described.

* * * * *